US007338941B2

(12) United States Patent
Bibbs et al.

(10) Patent No.: US 7,338,941 B2
(45) Date of Patent: Mar. 4, 2008

(54) PHARMACEUTICAL COMPOSITIONS FOR LOWERING BLOOD GLUCOSE AND BLOOD CHOLESTEROL LEVELS

(75) Inventors: Jeffrey A. Bibbs, San Diego, CA (US); Srirama Rao, San Diego, CA (US)

(73) Assignee: Diakron Pharmaceuticals, Inc., Morris Plains, NJ (US)

( * ) Notice: Subject to any disclaimer, the term of this patent is extended or adjusted under 35 U.S.C. 154(b) by 0 days.

(21) Appl. No.: 10/426,241

(22) Filed: Apr. 28, 2003

(65) Prior Publication Data

US 2004/0006128 A1 Jan. 8, 2004

Related U.S. Application Data

(60) Provisional application No. 60/378,716, filed on May 6, 2002.

(51) Int. Cl.
*A61K 31/70* (2006.01)
*A61K 31/7028* (2006.01)
*A61K 31/7042* (2006.01)

(52) U.S. Cl. .................. 514/27; 514/25; 514/456; 536/4.1

(58) Field of Classification Search .......... 514/27, 514/23, 456, 25; 536/4.1
See application file for complete search history.

(56) References Cited

FOREIGN PATENT DOCUMENTS

| EP | 0 775 451 A1 | | 5/1997 |
|---|---|---|---|
| JP | 01179678 | * | 7/1989 |
| JP | 01179678 A | * | 7/1989 |
| WO | WO 00/59522 | | 10/2000 |

OTHER PUBLICATIONS

Lamba et al. (Studies in Natural Products chemistry (2000), 21 (Bioactive Natural Products (Part B), 457-496)) (Abstract Sent).*
Easa et al. (International journal of Chemistry (1995), 6 (1 &2), 21-25) (Abstract sent).*
Vasilenko et al. (Izvestyia Severo-Kavkaskogo Nauchnogo Tsentra Vysshei Shkoly, Estestvvennye Nauki (1978), 6(40), 99-101) (Abstract sent).*
Rastrelli et al. (Journal of Natural Products (2001), 64 (1), 79-81).*
Sharma et al. (European Journal of Clinical Nutrition, (Apr. 1990) 44 (4), pp. 301-306 (Abstract Sent).*
Sishadri et al. (Current Science (1973), 43 (12), 421-2) (Abstract Sent).*
Abstract of Ramaratonamu et al., JP 01179678A, Jul. 17, 1989 (Abstract sent).*
Bellman et al. (Helvetica Chimica Acta (1973), 56(1), 284-294) (Abstract Sent).*
Ramaratonamu et al.; JP 01179678, Jul. 17, 1989 (Abstract Sent).*
Abdel-Barry, J.A. et al., Hypoglycaemic effect of aqueous extract of the leaves of Trigonella foenum-graecum in healthy volunteers, East. Mediterr. Health. J. 6(1):83-88 (2000).

Anila, L. et al., Beneficial effects of flavonoids from *Sesamum indicum, Emblica officinalis* and *Momordica charantia*, Phytother. Res. 14(8):592-5 (2000).
Bhardwaj, P.K. et al., Control of hyperglycaemia and hyperlipidaemia by plant product, J. Assoc. Physicians India 42(1):33-35 (1994).
Bhatti, M.A. et al., Antibacterial activity of trigonella foenum-graecum seeds, Fitoterapia 67:372-374 (1996).
Bordia, A. et al., Effect of ginger (*Zingiber officinale* Rosc.) and fenugreek (*Trigonella foenumgraecum* L.) on blood lipids, blood sugar and platelet aggregation in patients with coronary artery disease, Prostaglandins Leukot. Essent. Fatty Acids 56(5):379-84 (1997).
Exner, M. et al., Genistein prevents the glucose autoxidation mediated atherogenic modification of low density lipoprotein, Free Radic. Res. 34(1):101-12 (2001).
Guillot, R. et al. Effect of long-term treatment with a purified micronized flavonoid fraction on pancreatic mononuclear cell infiltration in diabetic BB rats, Pancreas 17(3):301-8 (1998).
Hii, C.S. et al., Effects of epicatechin on rat islets of Langerhans, Diabetes 33(3):291-6 (1984).
Hollman, P.C. et al., The sugar moiety is a major determinant of the absorption of dietary flavonoid glycosides in man, Free Radic. Res. 31(6):569-73 (1999).
Kim, J.S., et al., Inhibition of alpha-glucosidase and amylase by luteolin, a flavonoid, Biosci. Biotechnol. Biochem. 64(11):2458-61 (2000).
Kumar, R.V. et al., Antidiabetic effect of a leucocyanidin derivative isolated from the bark of *Ficus bengalensis* linn., Indian J. Biochem. Biophys. 6:400-4 (1989).
Lean, M.E. et al., Dietary flavonols protect diabetic human lymphocytes against oxidative damage to DNA, Diabetes 48(1):176-81 (1999).
Lee, S.C. et al., Bioflavonoids commonly and potently induce tyrosine dephosphorylation/inactivation of oncogenic proline-directed protein kinase FA in human prostate carcinoma cells, Anti-cancer Res. 18(2A):1117-21 (1998).
Lim, S.S. et al., Synthesis of flavonoids and their effects on aldose reductase and sorbitol accumulation in streptozotocin-induced diabetic rat tissues, J. Pharm. Pharmacol. 53(5):653-68 (2001).
Lin, et al., Prevention of cellular ROS damage by isovitexin and related flavonoids, Planta Med. 68:365-367 (2002).
Lonchampt, M. et al., Protective effect of a purified flavonoid fraction against reactive oxygen radicals: In vivo and in vitro study, Arzneimittelforschung. 39(8):882-5 (1989).
Madar, Z. et al., Glucose-lowering effect of fenugreek in non-insulin dependent diabetics, Eur. J. Clin. Nutr. 42(1):51-4 (1988).
Madar, Z. et al., Dietary fiber, Prog. Food Nutr. Sci. 11(2):153-174 (1987).
Madar, Z., New sources of dietary fibre, Int. J. Obes. 11:57-65 (1987).
Morand, C. et al., Respective bioavailability of quercetin aglycone and its glycosides in a rat model, Biofactors 12:169-74 (2000).
Sadhukhan, B. et al., Clinical evaluation of a herbal antidiabetic product, J. Indian Med. Assoc. 92(4):115-7 (1994).

(Continued)

*Primary Examiner*—Shaojia Anna Jiang
*Assistant Examiner*—Michael C. Henry
(74) *Attorney, Agent, or Firm*—Knobbe, Martens, Olson & Bear LLP

(57) ABSTRACT

Methods of treating a mammal with high blood-glucose, or high blood-cholesterol, levels with isovitexin, and pharmaceutical compositions comprising the same are disclosed.

6 Claims, 1 Drawing Sheet

OTHER PUBLICATIONS

Sakushima, et al., Major antioxidative substances in *Boreava orientalis* (cruciferae), Natural Product Letters, 14(6):441-446 (2000).

Sharma, R.D. et al., Effect of fenugreek seeds on blood glucose and serum lipids in type I diabetes, European Journal of Clinical Nutrition 44:301-6 (1990).

Sharma, R. D. et al, Hypoglycaemic effects of Fenugreek seeds in non-insulin dependent diabetic subjects, Nutrition Research 10:731-79 (1990).

Sharma, R. D. et al., Hypolipidaemic effect of Fenugreek seeds: a chronic study in non-insulin dependent diabetic patients, Phytotherapy Research 10: 332-334 (1996).

Shin, et al., Synthesis and hypoglycemic effect of chrysin derivatives, Bioorganic and Medicinal Chemistry Letters, 9:869-874 (1999).

Soto, et al., Prevention of alloxan-induced diabetes mellitus in the rat by silymarin, Comp. Biochem. Physiol. 119(2):125-9 (1998).

Sowmya, P. et al., Hypocholesterolemic effect of germinated fenugreek seeds in human subjects, Plant Foods Hum. Nutr. 53(4):359-65 (1999).

Totte, et al., *Trigonella foenum-graecum* 1., Farmaceutisch Tijdschrift Voor Belgie, 60(4):203-215 (1983).

Wang, H.X. et al., Natural products with hypoglycemic, hypotensive, hypocholesterolemic, antiatherosclerotic and antithrombotic activities, Life Sci. 65(25):2663-77 (1999).

Zenon, G.J. 3rd, et al., Potential use of aldose reductase inhibitors to prevent diabetic complications, Clin. Pharm. 9(6):446-57 (1990).

* cited by examiner

PHARMACEUTICAL COMPOSITIONS FOR LOWERING BLOOD GLUCOSE AND BLOOD CHOLESTEROL LEVELS

RELATED APPLICATIONS

The present application is related to and claims priority to the U.S. Provisional Application Ser. No. 60/378,716, filed May 6, 2002, by Bibbs et al., and entitled "PHARMACEUTICAL COMPOSITIONS FOR LOWERING BLOOD GLUCOSE AND BLOOD CHOLESTEROL LEVELS," the entire disclosure of which, including any drawings, is hereby incorporated by reference herein.

BACKGROUND OF THE INVENTION

1. Field of the Invention

The present invention relates to the field of lowering blood glucose or blood cholesterol levels by administering a bioflavanoid to a mammal in need thereof.

2. Description of the Related Art

Diabetes mellitus is a chronic condition characterized by the inability to regulate blood glucose levels. It is estimated that 1.5 to 2% of the entire population of the world suffers from diabetes mellitus of some type. Diabetes mellitus is a metabolic disorder of the human body primarily involving an inability of the body to properly store and utilize sugar and other chemical compounds in the metabolism of the body. It is characterized by an elevation in the concentration of sugar in the blood and also by the appearance of sugar in the urine.

In general terms, diabetes mellitus is classified into three types, namely, Type I and Type II. In Type I diabetes, the beta cells in the pancreas, probably through an auto-immune reaction, cease production and secretion of insulin into the bloodstream. Insulin is a hormone that is normally secreted into the bloodstream by beta cells within the pancreas. Insulin enables the body to properly utilize and store (as fat) the sugars that enter the bloodstream as part of the digestive process.

In Type I cases, where the pancreas has ceased producing insulin, it is necessary for the patient to directly inject insulin at prescribed periodic intervals and dosages in order to maintain control of the level of sugar in the blood.

In Type I and Type II diabetes, the pancreas continues to produce insulin but, some or all of the insulin may fail to bind to the body's cell receptors and/or internalization of insulin in the cells is reduced. In such cases, there may be a sufficient level of insulin in the blood, but the ability of the cells to uptake glucose is reduced or non-existent because of reduced internalized insulin. There is a significant need for new pharmaceutical agents that will facilitate regulation of blood sugar, without the necessity for insulin injections.

SUMMARY OF THE INVENTION

Disclosed is a method of treating a mammal with a high blood glucose level or high blood cholesterol level comprising (a) identifying a mammal in need of said treatment; and (b) administering to the mammal an effective amount of isovitexin or a pharmaceutically acceptable salt, ester, amide, or prodrug thereof.

Also disclosed is a method of treating a mammal with a high blood glucose level high blood cholesterol level comprising (a) identifying a mammal in need of said treatment; and (b) contacting the blood of said mammal with an effective amount of isovitexin or a pharmaceutically acceptable salt, ester, amide, or prodrug thereof.

Further, a pharmaceutical composition is disclosed comprising isovitexin or a pharmaceutically acceptable salt, ester, amide, or prodrug thereof, and a physiologically acceptable carrier, diluent, or expedient. Similarly, derivative and related compounds sharing some structural similarity with isovitexin are disclosed, that are useful in the methods and compositions disclosed herein In addition, many of these compounds are new chemical entities.

DETAILED DESCRIPTION OF THE PREFERRED EMBODIMENT

Figure 1:
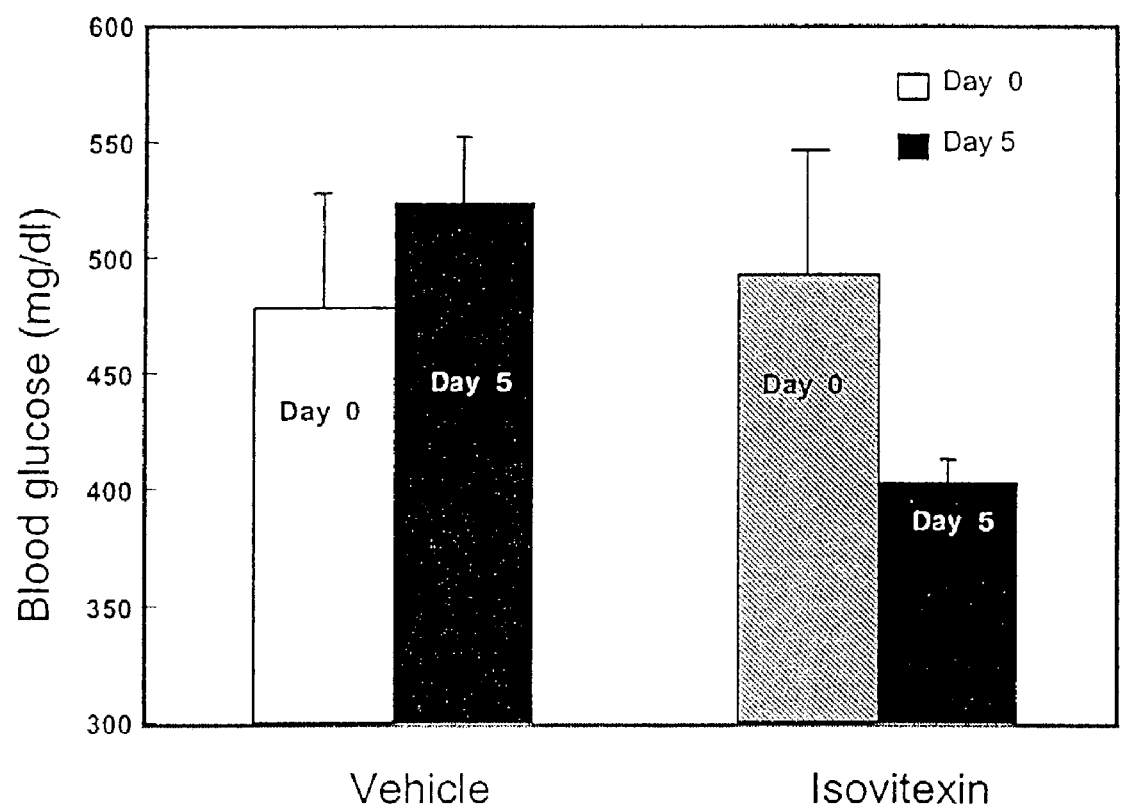
FIG. 1 shows the effect of oral administration of isovitexin on blood glucose levels.

We have discovered that isovitexin, a naturally occurring 7-O-beta-D-glucoside bioflavonoid with known antioxidant and anti-inflammatory properties, is a molecule with potent anti-diabetic activity in a murine model of Type II diabetes. Isovitexin is also capable of lowering the blood cholesterol levels of mammals. Certain other bioflavonoids, with certain structural similarities with isovitexin, also exhibit blood-glucose and blood-cholesterol lowering properties.

Thus, in a first aspect, the invention relates to a method of treating a mammal with a high blood glucose level comprising a) identifying a mammal in need of said treatment; and b) administering to said mammal a composition comprising an effective amount of isovitexin or a pharmaceutically acceptable salt, ester, amide, or prodrug thereof, where the composition comprises less than 50% of other naturally occurring bioflavanoids.

In some embodiments, the administered composition comprises less than 40% of other naturally occurring bioflavanoids, while in other embodiments, the composition comprises less than 35% of other naturally occurring bioflavanoids. In yet other embodiments, the composition comprises less than 30%, less than 25%, less than 20%, less than 15%, or less than 10% of other naturally occurring bioflavanoids. In certain embodiments, the composition comprises less than 5% of other naturally occurring bioflavanoids.

In some embodiments, the isovitexin is isolated from a natural source, whereas in other embodiments, the isovitexin is synthetic.

In another aspect, the invention relates to a method of treating a mammal with a high blood glucose level comprising a) identifying a mammal in need of said treatment; and b) contacting the blood of said mammal with an effective amount of isovitexin or a pharmaceutically acceptable salt, ester, amide, or prodrug thereof.

In a further aspect, the invention relates to a method of treating a mammal with a high blood cholesterol level comprising a) identifying a mammal in need of said treatment; and b) administering to said mammal an effective amount of isovitexin or a pharmaceutically acceptable salt, ester, amide, or prodrug thereof.

In an additional aspect, the invention relates to a method of treating a mammal with a high blood cholesterol level comprising a) identifying a mammal in need of said treatment; and b)contacting the blood of said mammal with an effective amount of isovitexin or a pharmaceutically acceptable salt, ester, amide, or prodrug thereof.

Furthermore, aspects of the invention are related to a pharmaceutical composition comprising isovitexin or a pharmaceutically acceptable salt, ester, amide, or prodrug thereof, and a physiologically acceptable carrier, diluent, or expedient.

In certain embodiments, the mammal may be selected from the group consisting of mice, rats, rabbits, guinea pigs, dogs, cats, sheep, goats, cows, primates, such as monkeys, chimpanzees, and apes. In preferred embodiments, the mammal may be a human.

The term "pharmaceutically acceptable" refers to a formulation of a compound that does not cause significant irritation to an organism to which it is administered and does not abrogate the biological activity and properties of the compound.

Pharmaceutically acceptable salts can be obtained by reacting a compound, such as isovitexin, with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like.

The term "ester" refers to a chemical moiety with formula —(R)$_n$—COOR', where R and R' are independently selected from the group consisting of alkyl, cycloalkyl, aryl, heteroaryl (bonded through a ring carbon) and heteroalicyclic (bonded through a ring carbon), and where n is 0 or 1.

An "amide" is a chemical moiety with formula —(R)$_n$—C(O)NHR' or —(R)$_n$—NHC(O)R', where R and R' are independently selected from the group consisting of alkyl, cycloalkyl, aryl, heteroaryl (bonded through a ring carbon) and heteroalicyclic (bonded through a ring carbon), and where n is 0 or 1. An amide may be an amino acid or a peptide molecule attached to a molecule of the present invention, thereby forming a prodrug.

Any amine, hydroxy, or carboxyl side chain on isovitexin or a derivative thereof can be esterified or amidified. The procedures and specific groups to be used to achieve this end is known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein in its entirety.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be isovitexin, or a derivative thereof, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety.

I. Isolation of Isovitexin

Isovitexin, also known as 4H-1-benzopyran-4-one, 6-β-D-glucopyranosyl-5,7-dihydroxy-2-(4-hydroxyphenyl), is a bioflavanoid having the following structure.

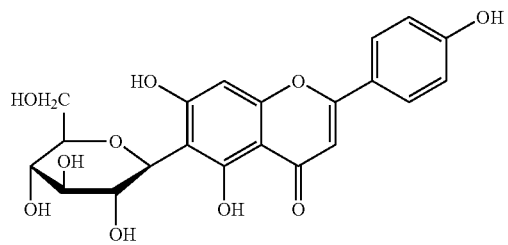

It is commercially available from Sigma-Aldrich (Milwaukee, Wis.) (Fluka Cat. #17804), among other vendors. Analytical data of extracts obtained from fenugreek seeds, as discussed below, were compared with the same data of the commercially available isovitexin to determine that the extracts included isovitexin.

Earlier studies (unpublished results) demonstrated that the water extract of fenugreek seeds followed by ion exchange, gel filtration, and thin layer chromatography (TLC) results in an extract that contained an unidentified bioactive compound that has potent glucose lowering activity when administered to alloxan-induced diabetic rabbits. Aspects of the present invention relate to the identification and characterization of the bioactive component(s) in this TLC derived fraction. HPLC analysis of the TLC derived fraction revealed the presence of two peaks with differing mobility's. Based on the retention time of the two peaks, a simple one step chromatographic method of isolation of these two peaks by HPLC was developed. The chemical structure of the second peak (DP-1032T) was resolved and it was identified by NMR as "isovitexin" (see details below).

II. Isovitexin Analogs

As mentioned above, a derivative of isovitexin can be used in the methods of the present invention. Examples of some of the derivatives that are useful for the methods of the invention include those that have the following structure and combinations thereof:

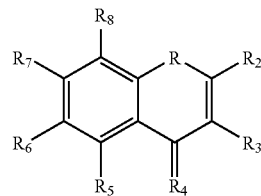

where

R and $R_4$ are each independently selected from the group consisting of oxygen, sulfur, $SiH_2$, NH, and $CH_2$;

$R_2$ is selected from the group consisting of 2-hydroxyphenyl, 3-hydroxyphenyl, 4-hydroxyphenyl, 2-methoxyphenyl, 3-methoxyphenyl, 4-methoxyphenyl, 2-ethoxyphenyl, 3-ethoxyphenyl, 4-ethoxyphenyl, 2-propoxyphenyl, 3-propoxyphenyl, 4-propoxyphenyl, 2-isopropoxyphenyl, 3-isopropoxyphenyl, 4-isopropoxyphenyl, 2-butoxyphenyl, 3-butoxyphenyl, 4-butoxyphenyl, 2-tert-butoxyphenyl, 3-tert-butoxyphenyl, 4-tert-butoxyphenyl, 2-trifluoromethoxyphenyl, 3-trifluoromethoxyphenyl, 4-trifluoromethoxyphenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 3-iodophenyl, 4-iodophenyl, 2-phenylacetate, 3-phenylacetate, 4-phenylacetate, 2-tetrahydropyran-2-oxy-phenyl, 3-tetrahydropyran-2-oxy-phenyl, 4-tetrahydropyran-2-oxy-phenyl, 2-methoxymethoxyphenyl, 3-methoxymethoxyphenyl, 4-methoxymethoxyphenyl, 2-methoxyethoxymethoxyphenyl, 3-methoxyethoxymethoxyphenyl, and 4-methoxyethoxymethoxyphenyl;

$R_3$ is selected from the group consisting of hydrogen, fluoro, chloro, bromo, and iodo;

$R_5$ and $R_7$ are each independently selected from the group consisting of hydroxy, methoxy, propoxy, isopropoxy, butoxy, tert-butoxy, trifluoromethoxy, methoxymethoxy, methoxyethoxymethoxy, methylthiomethoxy, fluoro, chloro, bromo, iodo, amino, methylamino, propylamino, butylamino, tert-butylamino, dimethylamino, dipropylamino, dibutylamino, di-tert-butylamino, acetoxy, and trifluoroacetoxy; and $R_6$ and $R_8$ are each independently selected from the group consisting of hydrogen, glucose, a monosaccharide, and a disaccharide;

Those of skill in the art know how to make the derivatives using conventional organic chemistry synthetic schemes.

III. Mechanism of Isovitexin Activity

Isovitexin, a naturally occurring 7-O-beta-D-glucosides bioflavonoid with known anti-oxidant and anti-inflammatory properties, was initially isolated from water soaked fenugreek seeds by reversed-phase HPLC. This molecule demonstrates a hitherto uncharacterized orally available glucose lowering activity in animals has the potential for treatment of diabetes (both type II, and perhaps type I) in humans. The mode of action of isovitexin lowering blood glucose and cholesterol is currently unknown. However, isovitexin may be active through a number of different mechanisms that include but are not limited to:

1. Increased insulin sensitivity. Since db/db obese mice have elevated levels of insulin levels circulating in their plasma, these mice have often been used as a model to assess the efficacy of drugs as insulin sensitizers. DP-1032T can function as insulin sensitizers. Thiazolidinediones, such as rosiglitazone maleate (AVANDIA®), act as insulin sensitizers, by working as agonists for proliferator-activated receptor gamma (PPARγ). PPAR gamma is a ligand-activated transcription factor and functions as a heterodimer with a retinoid X receptor. Activation of PPAR gamma by thiazolidinediones can reduce insulin resistance and hyperglycemia in type 2 diabetes, 2. Increased insulin secretion and pancreatic function. Naturally occurring flavonoids have been reported to protect pancreatic beta cells (1) and to stimulate beta cell regeneration [2,3].

3. Function as aldose reductase inhibitors (ARIs). ARIs are a new class of drugs potentially useful in preventing diabetic complications, the most widely studied of which have been cataracts and neuropathy. ARIs inhibit aldose reductase, the first, rate-limiting enzyme in the polyol metabolic pathway (see reference 12). ARIs are a class of structurally dissimilar compounds that include carboxylic acid derivatives, flavonoids, and spirohydantoins. The major pharmacologic action of an ARI involves competitive binding to aldose reductase and consequent blocking of sorbitol production.

4. Bioflavonoids commonly and potently induce tyrosine dephosphorylation/inactivation of oncogenic proline-directed protein kinase FA in human prostate carcinoma cells [15]. It is conceivable that isovitexin could induce tyrosine dephosphorylation/inactivation of protein kinase to induce glucose lowering effects.

IV. Pharmaceutical Compositions

The present invention also relates to a pharmaceutical composition comprising
  a) a compound of the invention as described herein; and
  b) a pharmaceutically acceptable carrier, diluent, or excipient, or a combination thereof.

The term "pharmaceutical composition" refers to a mixture of a compound of the invention with other chemical components, such as diluents or carriers. The pharmaceutical composition facilitates administration of the compound to an organism. Multiple techniques of administering a compound exist in the art including, but not limited to: oral, injection, aerosol, parenteral, and topical administration. Pharmaceutical compositions can also be obtained by reacting compounds with inorganic and organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemicals used to dilute the compound that will allow for consistent administration as well as stabilize the biologically active form of the compound. One commonly used liquid diluent is phosphate buffered saline and another commonly used solid diluent is lactose. Diluents rarely modifies the biological activity of a compound.

The term "physiologically acceptable" defines a carrier or diluent that does not abrogate the biological activity and properties of the compound.

The compounds described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

a) Routes of Administration

Suitable routes of administration may, for example, include oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections.

Alternately, one may administer the compound in a local rather than systemic manner, for example, via injection of the compound directly into a solid tumor, often in a depot or sustained release formulation. Furthermore, one may administer the drug in a targeted drug delivery system, for example, in a liposome coated with tumor-specific antibody. The liposomes will be targeted to and taken up selectively by the tumor.

b) Composition/Formulation

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by mixing one or more solid excipient with one or more compound of the invention, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethyl cellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant Polysorbate 80™, and 65% w/v polyethylene glycol 300, made up to volume in absolute ethanol. The VPD co-solvent system (VPD:D5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free acid or base forms.

c) Effective Dosage.

Pharmaceutical compositions suitable for use in the present invention include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

For any compound used in the methods of the invention, the therapeutically effective dose can be estimated initially from cell culture assays. For example, a dose can be formulated in animal models to achieve a circulating concentration range that includes the $IC_{50}$ as determined in cell culture. Such information can be used to more accurately determine useful doses in humans.

Toxicity and therapeutic efficacy of the compounds described herein can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used to calculate a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g., Fingl et al. 1975, in "The Pharmacological Basis of Therapeutics", Ch. 1 p. 1). Typically, the dose range of the composition administered to the patient can be from about 0.5 to 1000 mg/kg of the patient's body weight. The dosage may be a single one or a series of two or more given in the course of one or more days, as is needed by the patient.

Dosage amount and interval may be adjusted individually to provide plasma levels of the active moiety which are sufficient to maintain the kinase modulating effects, or minimal effective concentration (MEC). The MEC will vary for each compound but can-be estimated from in vitro data; e.g., the concentration necessary to achieve 50-90%, inhibition of the kinase using the assays described herein. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

d) Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the polynucleotide for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

EXAMPLES

The examples below are non-limiting and are merely representative of various aspects of the invention.

Example 1

Animal Model and Assessment of Blood-Sugar-Lowering Activity of Isovitexin

Db/db mice are commonly used as an in vivo model for studying type II diabetes in animals. Db/db (C57BLKS/J-m+/+Lepr$^{db}$) obese mice are obtained from Jackson Laboratories (Maine) and maintained in a temperature-controlled (25° C.) facility with a strict 12-h light/dark cycle and given free access to food and water. Mice are fed pelleted rodent chow which is low in fat (4% w/w). Fasting mice are orally administered with isovitexin dissolved in aqueous vehicle containing 50% PEG50% (10 mg/kg body weight) in a total volume of 200 µL or vehicle alone daily for 5 days. Food is removed from mice 4 hours before the collection of blood from the tail vein. Blood is obtained from mice by drawing one drop of blood (~50 μL) from the tail vein for glucose analysis. Blood glucose is analyzed using a digital glucometer.

Db/db obese mice (n=3: test; n=4: vehicle) were treated daily with 200 μL of isovitexin dissolved in an aqueous solution of PEG 50% (10 mg/kg body weight) or vehicle alone for 5 days. Blood glucose was estimated on day 0, one day prior to initiation of the treatment and on day 5, four hours after withdrawal of food. Blood was obtained from mice by drawing one drop of blood (~50 μL) from the tail vein for glucose analysis. Blood glucose was analyzed using a digital glucometer and performed in duplicate. Blood glucose values are described as mg/dL±SD. The blood glucose levels in the vehicle treated group (n=4) were 446±35 on day 0 and 477±48 on day 5. In contrast, oral treatment with isovitexin resulted in reduction of blood glucose levels from 493±54 on day 0 to 404±10 on day 5. While treatment with DP-1032T resulted in a ~17.8% reduction in blood glucose, blood glucose levels in the vehicle treated group increased by ~11.9%. The results are summarized in Tables 1 and 2 below, and FIG. 1.

TABLE 1

Effect of oral administration of isovitexin on blood glucose levels (mg/dl ± SD) in db/db mice

| Group 1 | Before treatement (day 0) | After treatment with isovitexin (day 5) |
|---|---|---|
| Mouse 1: | 554 ± 7.07 | 415 ± 21.9 |
| Mouse 2: | 451 ± 21 | 396 ± 2.12 |
| Mouse 3: | 473 ± 6.36 | 400 ± .71 |

| Group 2 | Before Treatment (day 0) | After treatment with vehicle (day 5) |
|---|---|---|
| Mouse 1: | 431 ± 2.83 | 423 ± 2.8 |
| Mouser 2: | 447 ± 31.1 | 479 ± 11.3 |
| Mouse 3: | 494 ± 6.36 | 466 ± 5.6 |
| Mouse 4: | 411.5 ± 6 | 540 ± 0.7 |

TABLE 2

Percent change in blood glucose levels after treatment with Isovitexin

| Group | % change in blood glucose after 5 days of treatment |
|---|---|
| Vehicle | 11.9 ± 13.4 (increase) |
| Isovitexin | 17.8 ± 7.21 (decrease) |

These results indicate that isovitexin is effective in lowering of blood glucose in db/db mice. While the dosage used was 10 mg/kg body weight, a higher dosage results in a greater decrease in blood glucose. Also, a longer term usage of the drug lowers blood glucose levels to the normal values observed in mice.

Example 2

Animal Model and Assessment of Blood-Sugar-Lowering Activity of an Isovitexin Analog The procedures described in Example 1 are repeated using an isovitexin-analog as described herein.

Example 3

Animal Model and Assessment of Cholesterol-Lowering Activity of Isovitexin

Mice are obtained from Jackson Laboratories (Maine) and maintained in a temperature-controlled (25° C.) facility with a strict 12-h light/dark cycle and given free access to food and water. Mice are fed pelleted rodent chow which is low in fat (4% w/w). One group of fasting mice are orally administered with isovitexin dissolved in aqueous vehicle containing 50% PEG50% (10 mg/kg body weight) in a total volume of 200 μL, while another group is administered the vehicle. Isovitexin, or vehicle, is given daily for 5 days. Food is removed from mice 4 hours before the collection of blood from the tail vein. Blood is obtained from mice by drawing one drop of blood (~50 μL) from the tail vein for cholesterol level analysis.

Example 4

Animal Model and Assessment of Cholesterol-Lowering Activity of an Isovitexin Analog The procedures described in Example 3 are repeated using an isovitexin-analog as described herein.

REFERENCES

All of the following references are incorporated by reference herein in their entirety, including any drawings.
1. Soto, et al., "Prevention of alloxan-induced diabetes mellitus in the rat by silymarin," Comp Biochem Physiol C Pharnacol Toxicol Endocrinol 1998 Feb; 119(2):125-9.
2. Lean M E, et al., "Dietary flavonols protect diabetic human lymphocytes against oxidative damage to DNA," Diabetes 1999 Jan; 48(1):176-81.
3. Wang H X, et al., "Natural products with hypoglycemic, hypotensive, hypocholesterolemic, antiatherosclerotic and antithrombotic activities," Life Sci. 1999;65(25): 2663-77.
4. Exner M, et al., "Genistein prevents the glucose autoxidation mediated atherogenic modification of low density lipoprotein," Free Radic Res. 2001 Jan; 34(1):101-12.
5. Lim S S, et al., "Synthesis of flavonoids and their effects on aldose reductase and sorbitol accumulation in streptozotocin-induced diabetic rat tissues," J Pharm Pharmacol 2001 May; 53(5):653-68.
6. Kim J S, et al., "Inhibition of alpha-glucosidase and amylase by luteolin, a flavonoid," Biosci Biotechnol Biochem 2000 Nov; 64(11):2458-61.
7. Guillot R, et al. "Effect of long-term treatment with a purified micronized flavonoid fraction on pancreatic mononuclear cell infiltration in diabetic BB rats," Pancreas 1998 Oct; 17(3):301-8.
8. Anila L, et al., "Beneficial effects of flavonoids from *Sesamum indicum, Emblica officinalis* and *Momordica charantia*," Phytother Res 2000 Dec; 14(8):592-5.
9. Hii C S, et al., "Effects of epicatechin on rat islets of Langerhans," Diabetes March 1984;33(3):291-6.
10. Morand C, et al., "Respective bioavailability of quercetin aglycone and its glycosides in a rat model," Biofactors 2000;12(1-4):169-74.

11. Hollman P C, et al., "The sugar moiety is a major determinant of the absorption of dietary flavonoid glycosides in man," Free Radic Res 1999 Dec; 31(6):569-73.
12. Zenon G J 3rd, et al., "Potential use of aldose reductase inhibitors to prevent diabetic complications," Clin Pharm. 1990 Jun; 9(6):446-57.
13. Lonchampt M, et al., "Protective effect of a purified flavonoid fraction against reactive oxygen radicals. In vivo and in vitro study," Arzneimittelforschung. 1989 Aug; 39(8):882-5.
14. Kumar R V, et al., "Antidiabetic effect of a leucocyanidin derivative isolated from the bark of *Ficus bengalensis Linn*," Indian J Biochem Biophys 1989, 6:400-4.
15. Lee S C, et al., "Bioflavonoids commonly and potently induce tyrosine dephosphorylation/inactivation of oncogenic proline-directed protein kinase FA in human prostate carcinoma cells," Anticancer Res. 1998 Mar.-Apr.; 18(2A): 1117-21.
16. Madar Z, et al., "Glucose-lowering effect of fenugreek in non-insulin dependent diabetics," Eur J Clin Nutr 1988 Jan; 42(1):51-4
17. Sharma, R. D. et al, "Effects of Fenugreek seeds in non-insulin dependent diabetes," Nutrition Research 1990, 10: 731-79.
18. Sharma R D, et al., "Effect of fenugreek seeds on blood glucose and serum lipids in type I diabetes," European Journal of Clinical Nutrition. 44:301-6, 1990.
19. Bordia A, et al. "Effect of ginger (*Zingiber officinale* Rosc.) and fenugreek (*Trigonella foenumgraecum L.*) on blood lipids, blood sugar and platelet aggregation in patients with coronary artery disease," Prostaglandins Leukot Essent Fatty Acids 1997 May; 56(5):379-84.
20. Sowmya P, Rajyalakshmi P., "Hypocholesterolemic effect of germinated fenugreek seeds in human subjects," Plant Foods Hum Nutr 1999;53(4):359-65.
21. Sharma, R. D. et al., "Hypolipidemic effect of Fenugreek seeds: a chronic study in Non-insulin Dependent Diabetic patients," Phytotherapy Research, 1996, 10: 332-334.
22. Sadhukhan B, et al., "Clinical evaluation of a herbal antidiabetic product," J Indian Med Assoc 1994 Apr; 92(4):115-7.
23. Bhardwaj P K, et al., "Control of hyperglycaemia and hyperlipidaemia by plant product," J Assoc Physicians India 1994 Jan; 42(1):33-35.
24. Abdel-Barry J A, et al., "Hypoglycaemic effect of aqueous extract of the leaves of *Trigonella foenumgraecum* in healthy volunteers," East Mediterr Health J. 2000 Jan; 6(1):83-8.
25. Madar Z., "New sources of dietary fibre," Int J Obes 1987;11:57-65.
26. Madar Z, Thome R., "Dietary fiber," Prog Food Nutr Sci 1987;11(2):153-174.

CONCLUSION

Thus, those of skill in the art will appreciate that new methods of lowering blood-glucose and blood-cholesterol levels in a patient are disclosed.

One skilled in the art will appreciate that these methods are and may be adapted to carry out the objects and obtain the ends and advantages mentioned, as well as those inherent therein. The methods and procedures described herein are presently representative of preferred embodiments and are exemplary and are not intended as limitations on the scope of the invention. Changes therein and other uses will occur to those skilled in the art which are encompassed within the spirit of the invention and are defined by the scope of the claims.

It will be apparent to one skilled in the art that varying substitutions and modifications may be made to the invention disclosed herein without departing from the scope and spirit of the invention.

Those skilled in the art recognize that the aspects and embodiments of the invention set forth herein may be practiced separate from each other or in conjunction with each other. Therefore, combinations of separate embodiments are within the scope of the invention as claimed herein.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Other embodiments are within the following claims.

What is claimed is:

1. A method of treating a mammal with a high blood glucose level comprising:
   (a) identifying a mammal in need of said treatment; and
   (b) administering to said mammal an effective amount of isolated isovitexin or a pharmaceutically acceptable salt, prodrug ester or prodrug amide thereof.

2. A method of treating a mammal with a high blood glucose level comprising:
   (a) identifying a mammal in need of said treatment; and
   (b) contacting the blood of said mammal with an effective amount of isolated isovitexin or a pharmaceutically acceptable salt, prodrug ester or prodrug amide thereof.

3. A method of treating a mammal with a high blood cholesterol level comprising:
(a) identifying a mammal in need of said treatment; and
(b) administering to said mammal an effective amount of isolated isovitexin or a pharmaceutically acceptable salt, prodrug ester or prodrug amide thereof.

4. A method of treating a mammal with a high blood cholesterol level comprising:
(a) identifying a mammal in need of said treatment; and
(b) contacting the blood of said mammal with an effective amount of isolated isovitexin or a pharmaceutically acceptable salt, prodrug ester, or prodrug amide thereof.

5. The method of any one of claims 1-4, wherein said mammal is selected from the group consisting of mice, rats, rabbits, guinea pigs, dogs, cats, sheep, goats, cows, primates, monkeys, chimpanzees, apes, and humans.

6. The method of claim 5, wherein said mammal is a human.

* * * * *